United States Patent [19]

Kay

[11] Patent Number: 4,592,750
[45] Date of Patent: Jun. 3, 1986

[54] OSTOMY APPLIANCE

[76] Inventor: Dennis M. Kay, 236 Mariner Dr., Tarpon Springs, Fla. 33589

[21] Appl. No.: 665,449

[22] Filed: Oct. 26, 1984

[51] Int. Cl.$^4$ ............................................. A61F 5/44
[52] U.S. Cl. ...................................... 604/337; 604/342
[58] Field of Search ................................. 604/332-345

[56] References Cited

U.S. PATENT DOCUMENTS

| | | | |
|---|---|---|---|
| 2,524,750 | 10/1950 | Bellinger | 604/334 |
| 2,542,233 | 2/1951 | Carroll | 604/337 |
| 2,544,579 | 3/1951 | Ardner | 604/337 |
| 2,721,553 | 10/1955 | Perry . | |
| 3,076,458 | 2/1963 | Mason . | |
| 3,283,757 | 11/1966 | Nelsen . | |
| 4,403,991 | 9/1983 | Hill . | |
| 4,439,191 | 3/1984 | Hogan | 604/337 X |

FOREIGN PATENT DOCUMENTS 533665  5/1958  Belgium ............................ 604/337

*Primary Examiner*—Harland S. Skogquist
*Attorney, Agent, or Firm*—Lalos, Keegan & Kaye

[57] ABSTRACT

An ostomy appliance including a faceplate having an inner surface, an opposite outer surface, and an opening engaging said inner surface. The faceplate is adapted to be placed so that its inner surface is generally against the body of the ostomate and the opening registers with the stoma of the user. The faceplate has outflow channels communicating with the opening and engaging the outer surface for allowing the outflow of stoma waste products from the stoma through the faceplate. A groove sealing arrangement attaches the receptacle to the faceplate and the stoma waste products flow through the outflow channels into the receptacle. A stoma protector shield having an inner shield surface adapted to face the user and an outer shield surface is positionable so that the inner shield surface is over the opening and spaced a small distance from the inner surface away from the user whereby a chamber is defined adjacent the stoma. The outflow channels communicate with the chamber. The protector shield which is positioned over the stoma protects the stoma when an object impacts the faceplate at a location. The shield can be removed from the faceplate so that irrigation and cleansing can be done through the faceplate while it is attached to the body. A vacuum can be created in the chambers of the suction faceplate embodiment causing it to adhere to the body.

36 Claims, 20 Drawing Figures

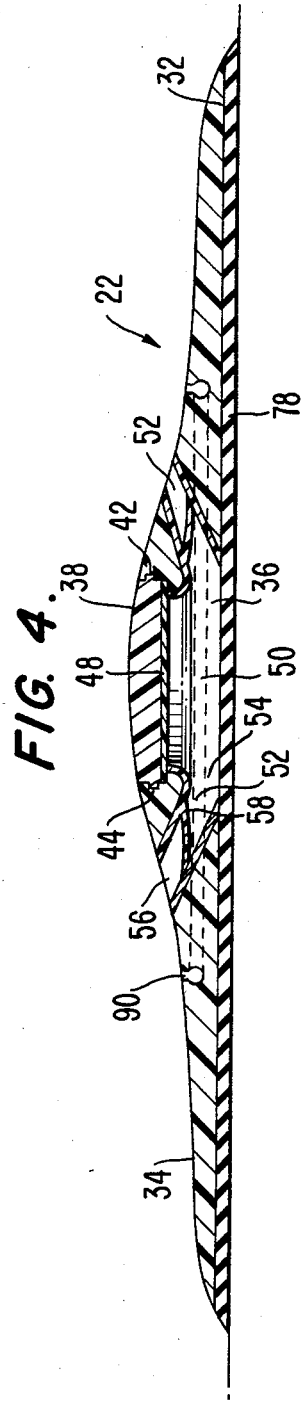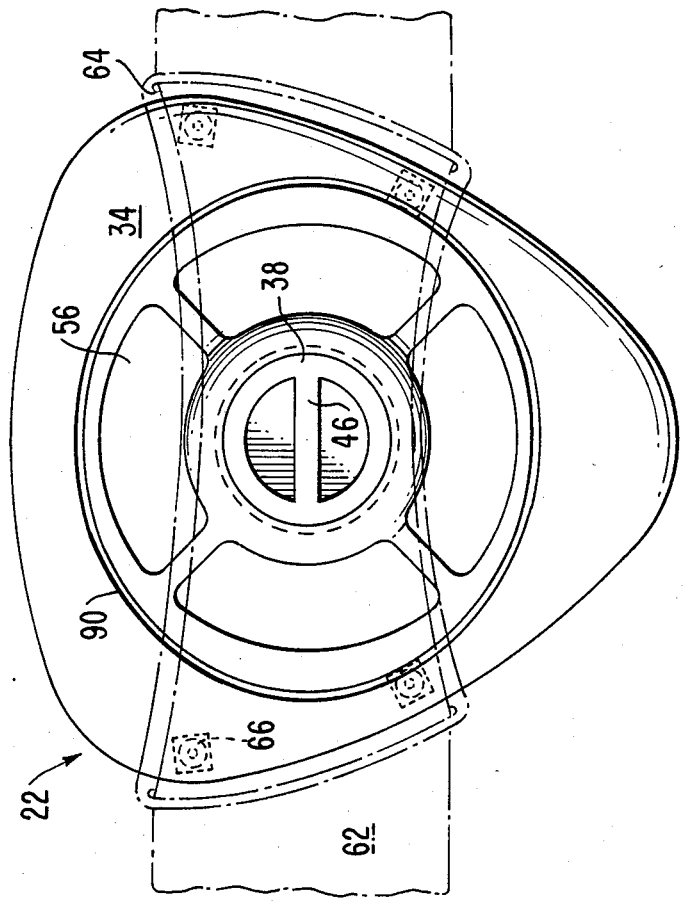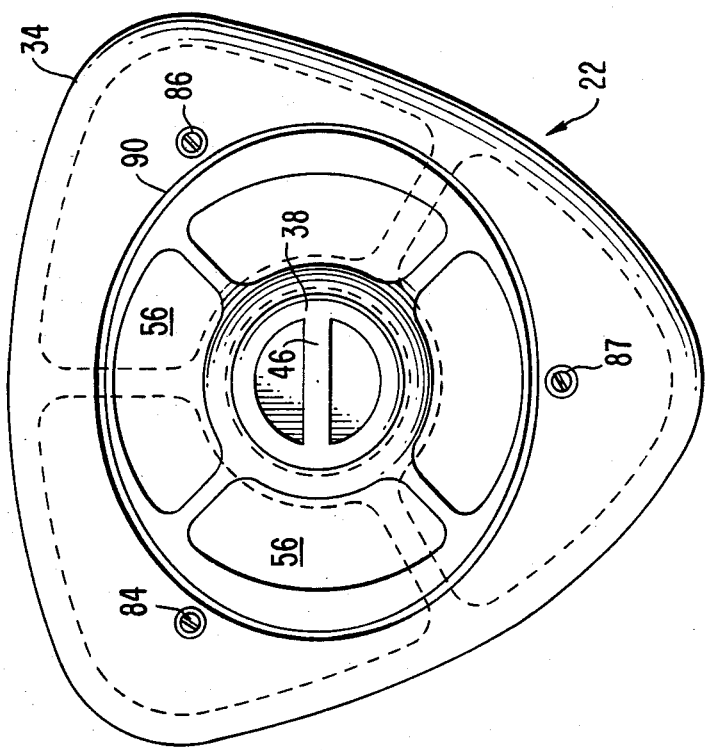

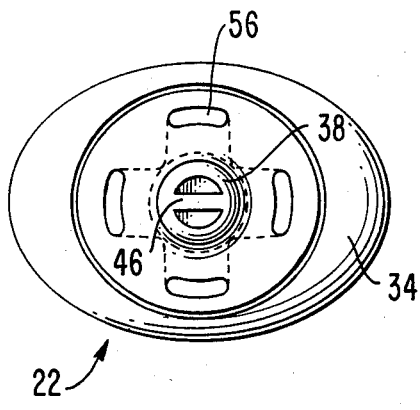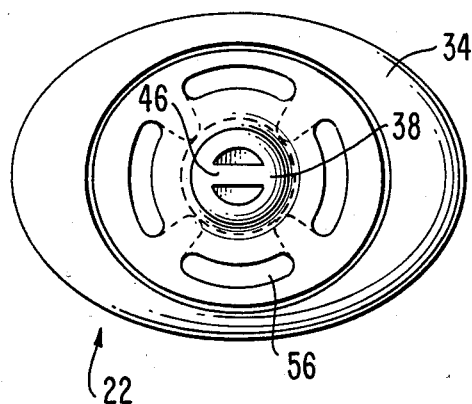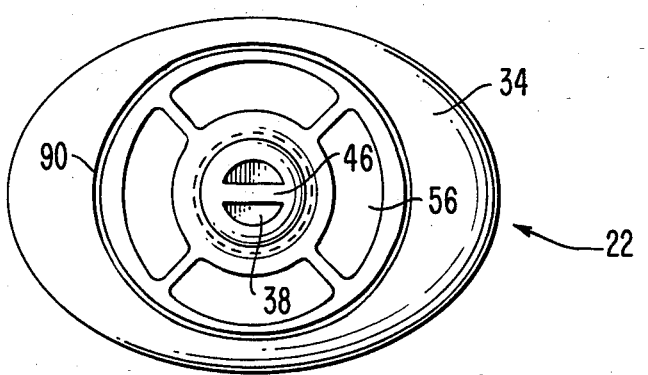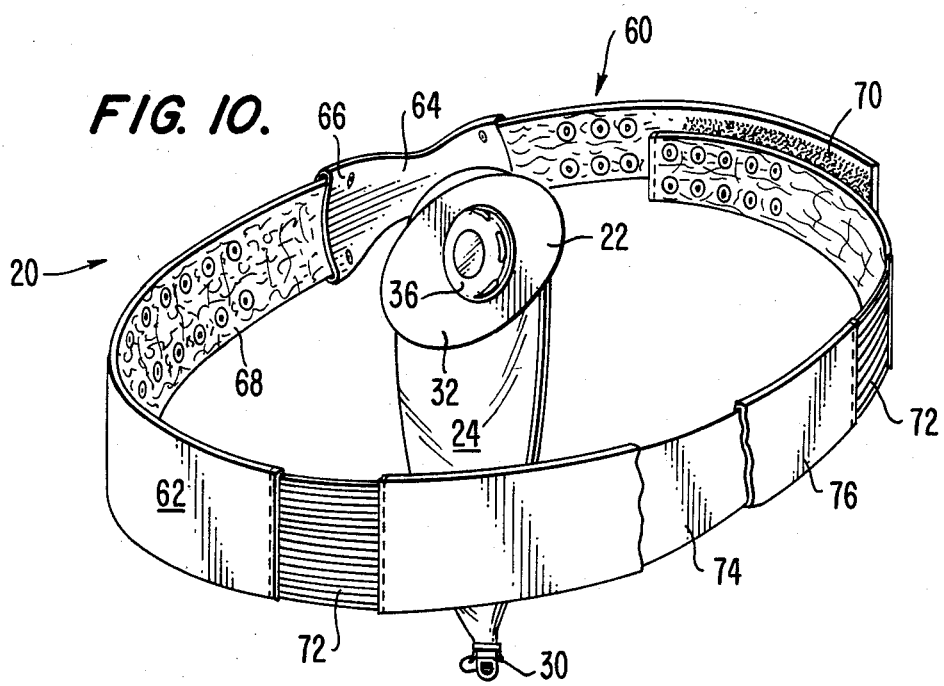

OSTOMY APPLIANCE

BACKGROUND OF THE INVENTION

The term "ostomy" is derived from the Latin word stoma, which means opening. The medical term "ostomy" refers to a variety of conditions in which either urinary or intestinal waste products are eliminated through an opening in the anterior abdominal wall (front of the abdomen). This opening in the abdominal wall is created as part of a variety of surgical procedures for the treatment of a number of different medical conditions. A colostomy, for example, is a surgically created route that allows the contents of the lower large intestine to pass out through an opening in the lower abdominal wall. An ileostomy is a similar surgically created opening through which the contents of the small intestine or ileum are allowed to drain out of the body. Urinary diversions, similarly, are created when an alternate route for the elimination of urine is required either due to a congenital defect or as surgical treatment for a disease process. Examples of urinary diversions include ureterostomies, urinary conduits or ureteroileostomies, all of which are collectively known as urostomies.

Ostomy surgery of all types was developed approximately 35 years ago. Indications for this surgery and frequency of usage increased as surgical techniques improved. The surgically created external drainage of body wastes requires an ostomy appliance, which is a receptacle for the collection of these wastes. The design and function of current ostomy appliances is based on their initial development over 30 years ago. Individuals now receive ostomy surgery with greater frequency, and these individuals are often younger or capable of increasing amounts of physical rehabilitation. Unfortunately, current ostomy products have not kept pace with the capabilities of modern ostomates. Present ostomy equipment fails to provide for the additional requirements of rehabilitation, long-term health and freedom of physical activity.

Current ostomy appliances consist of three basic components. (1) A faceplate is attached to the body wall around the stoma, generally with the use of adhesives and often with an adjunctive elastic belt. The faceplate usually stays in place from one to six days, depending on the appliance model, the patients skin condition and his level of activity. (2) A receptacle, which is attached to the faceplate, retains the intestinal or urinary waste products after they have passed through the stoma. (3) A drain is used to empty the receptacle when it becomes full.

A number of significant drawbacks are inherent in the designs of currently available ostomy products. These products lack provisions for psychological adjustment, privacy, security, ability to pursue a variety of physical activities, proper hygiene and prevention of infection, protection of the stoma and comfort.

Current ostomy products have not been designed with regard to the psychological adjustment required after ostomy surgery. Individuals dependent upon prosthetic devices including ostomates often have severe difficulty coping with or accepting their physical condition. This is an especially significant drawback for ostomates who may reject or ignore the existance of their ostomies. This self neglect can lead to poor hygiene, illness and diminished sense of self worth. These individuals may also feel that they are incapable of performing many activities of daily living and they therefore needlessly limit themselves.

Ostomy patients are deprived of privacy when wearing a current ostomy product with a thick bulky faceplate bulging through clothing, especially when the faceplate has an uneven external contour making its profile even more obvious. Current ostomy products with bulky drain valves and uneven contours can be uncomfortable against the patient's body and can make additional unsightly bulges in his clothing.

Security is a problem for the ostomy patient because waste products may leak unexpectedly and soil clothing or bedsheets. Most currently available ostomy faceplates are semi-rigid and secured to the surface of the body with adhesive and belts. These belts are narrow, and can curl up and dig into the wearer's skin. Although adhesive technology has improved considerably in the last 25 years, escape of waste products between the faceplate and the surface of the body is still the most common source of leakage in today's ostomy products. Additional leakage can occur between the faceplate and the receptacle, between the receptacle and the drain valve or through weak points in the receptacle.

Ostomy products are generally not designed to allow the pursuit of a variety of physical activities. Many modern ostomates have the physical health to allow them a full and active life. During active physical sports or sexual intercourse, current ostomy faceplates have a tendency to leak and become dislodged from the body wall. Simple activities such as baseball or racquetball can become embarrassing for the ostomate and actually dangerous for his or her stoma. Common daily activities such as wearing a seat belt or closely-tailored clothing can put pressure on the stoma and may be medically harmful when the outflow of waste products is artificially limited because of this external pressure. Experience has shown that this external pressure causes blockage of stoma outflow and may also cause reflux of excreted bodily wastes back into the body. With urostomies this stomal reflux and blockage plays an important role in causing recurrent urinary tract infections.

Current ostomy products also do not provide for easy access to the stoma for proper hygiene and prevention of infection. Chronic or recurrent infections are one of the leading causes of morbidity or illness in a long-term ostomate, especially those individuals with urinary diversions. All types of urostomies excrete mucus with the urinary wastes. This mucus tends to accumulate around the stoma and on the faceplate where, in the presence of urine and body heat, an excellent medium for bacterial growth is created. The concept of daily stoma care is unknown in the ostomy appliance industry and no currently available ostomy products make provisions for daily stoma hygiene. However, there should be daily cleansing of the stoma area when the entire ostomy appliance cannot be removed, as the present invention provides. For urinary diversions, a daily regimen that is designed to disinfect and cleanse the stoma, which is previously unknown, should markedly reduce the occurrence of chronic urinary diversion and upper urinary tract infections. Additionally, in individuals with stomas for elimination of intestinal waste, daily cleansing of the stoma and even enemas should be done.

It is further noted that currently available ostomy products do not protect the stoma from external injury or pressure. The stoma can be injured with relatively small force, and as noted above, during active physical activity there is a marked risk of injury to the stoma. Therefore current activities such as contact or ball sports are dangerous for the ostomate who uses current appliances. The stoma can also be injured accidentally, while coming in contact with hard or pointed surfaces during routine daily activities.

Comfort and the ability to be comfortable with an ostomy appliance is a major factor for all ostomates. Unfortunately, present ostomy products are remarkably lacking in provision for patient comfort. Comfort for the ostomate is composed of many factors: the internal contour of the faceplate as it fits the body, the external contour of the entire appliance as it appears beneath clothing, the materials used for the appliance, and the adhesives used. Many current ostomy appliance receptacle drain valves are bulky and made of hard materials. These valves can make unsightly bulges or if worn in the groin can cause injury during ordinary daily activities such as bicycling or horseback riding.

Comfort for the ostomate could be provided by custom design of the internal contour of the faceplate. Abdominal wall contour variations have two general categories. The general contour of the general abodominal wall can vary from one individual to another. Also, an individual's abdominal wall contour around the stoma can vary from point to point. The concept of varying the internal contour of an ostomy faceplate from side to side or top to bottom has not yet been pursued by the ostomy appliance industry. This requires a method to determine the variation of contours on each ostomate's abdomen, which the ostomy product industry currently does not have. Current ostomy products also have bulky irregular external contours which bulge through clothing. This is potentially uncomfortable and embarrassing.

Many currently available ostomy products are made of materials lacking in sufficient softness and flexibility for maximum comfort. Improved faceplate flexibility could allow maximal faceplate adherence and minimal leakage. There are no currently available ostomy products which provide optimal comfort via a highly flexible, soft faceplate with streamlined external contour and custom-designed internal contour.

Adhesives have improved since the initial development of ostomy products, but there is no currently available ostomy appliance which protects the stoma, has a smooth external contour and can be attached to the body without the use of adhesives. Adhesives necessitate a lengthy process of preparation for the attachment of the faceplate. Ostomy appliance adhesives and the chemicals required to prepare the skin for their application can cause severe recurrent or chronic irritation of the skin around the stoma, thus making the daily life of the ostomate more difficult and complicated.

In summary, there are many shortcomings and drawbacks among the wide variety of ostomy products currently available. The objects of the present invention are, thus, to improve psychological adjustment, privacy, security, ability to pursue a variety of physical activities, proper hygiene, prevention of infection, protection of the stoma and comfort for those who wear ostomy appliances. The products derived from the present invention will facilitate daily life for the ostomate and allow ostomy appliance wearers to pursue active, fulfilling and productive lives without any significant limitations of activity.

Other objects and advantages of the present invention will become more apparent to those persons having ordinary skill in the art to which the present invention pertains from the following description taken in conjunction with the accompanying drawings.

DESCRIPTION OF THE DRAWINGS

FIG. 4 is an enlarged cross-sectional view of the faceplate of FIG. 1.

FIG. 5 is a front view of an alternative triangular non-adhesive suction faceplate.

FIG. 6 is a front view of an alternative triangular non-adhesive faceplate having an overlying brace strap.

FIGS. 7-9 are front views of alternative elliptical faceplates for urostomy, ileostomy, and colostomy applications, respectively.

FIG. 10 is a perspective view of an ostomy appliance utilizing the brace strap system of the present invention.

DETAILED DESCRIPTION OF THE INVENTION

Figure 1:
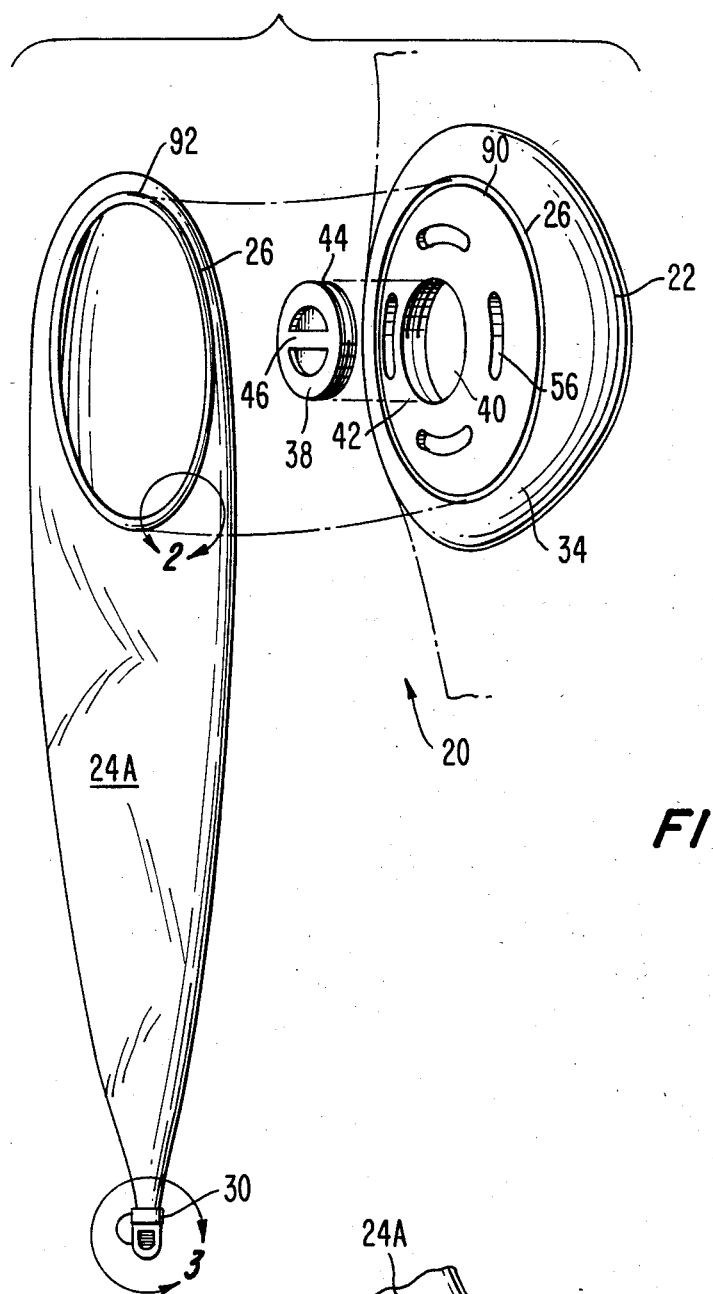
FIG. 1 is a perspective view of an ostomy appliance of the present invention having the parts thereof illustrated in exploded relation.

Referring to FIG. 1, an ostomy appliance embodying the present invention is shown generally at 20. Appliance 20 comprises generally a faceplate 22, a receptacle 24 attached by groove attachment means 26 to faceplate 22, and a drain valve 30 at the lower drain port end of receptacle 24 for draining the receptacle. Faceplate 22 is constructed of, referring to FIG. 4, a body of material having a lower surface 32, which alternatively can have a concave or convex shape to conform to different body contours, and an outer or upper surface 34. The triangular or eilliptical front shapes of the faceplate allow it to conform to the natural contours of the lower abdominal area thereby providing an easier and more secure attachment of the faceplate to the body for greater comfort and security. The faceplate also has a streamlined outer contour for greater comfort and privacy. The user can select the grade of flexibility of the material from which faceplate 22 is constructed for his maximum comfort, fit and range of body activities. It is further anticipated that all external surfaces of the faceplate that come into contact with urine will be Teflon coated for easy cleansing.

An opening 36 penetrates the faceplate lower surface 32 and faceplate 22 is positionable over the stoma of the user with opening 36 directly over the stoma. The openings for ileostomy and colostomy faceplates are larger than others to accommodate larger stoma sizes and semi-solid and solid intestinal waste products. A stoma protector shield 38 is positionable in an upper surface opening 40 in upper surface 34 of the faceplate. Upper surface opening 40 is positioned directly over and in communication with opening 36. Threaded members 42 are formed on the perimeter surface of upper surface opening 40 corresponding to the outer threaded members 44 of stoma protector shield 38. The protector shield can then be screwed or threaded into its position by grasping and turning its outer handle 46. When in position it protects the stoma during a wide range of daily and vigorous physical activity. Protector shield 38 further prevents impedence of the outflow of stoma waste products, such as has been caused in the past by seat belts, tight fitting clothing, close contact, and sports. Protector shield 38 can be later unscrewed or unsnapped from upper surface opening 40 by grasping handle 46, as shown in FIG. 1, and access is conveniently provided to the stoma and the adjacent inner faceplate for irrigating and daily hygiene while faceplate 22 is secured in place directly over the stoma. This feature is not present in currently available ostomy appliances. As previously noted, urinary diversion mucus tends to adhere to the stoma, faceplate, and receptacle, acting as an excellent medium for bacterial growth. Stoma and ostomy appliance hygiene on a daily basis, such as is possible with the present removable protector shield 38, eradicates peristomal and appliance mucus accumulation. This concept of daily stoma hygiene now possible can improve and maintain a healthy condition for the stoma tissues and in urinary diversions may be the intergral factor for the reduction of chronic urinary tract infections, thereby significantly decreasing the primary source of morbidity for individuals with urinary diversions.

Figure 14:
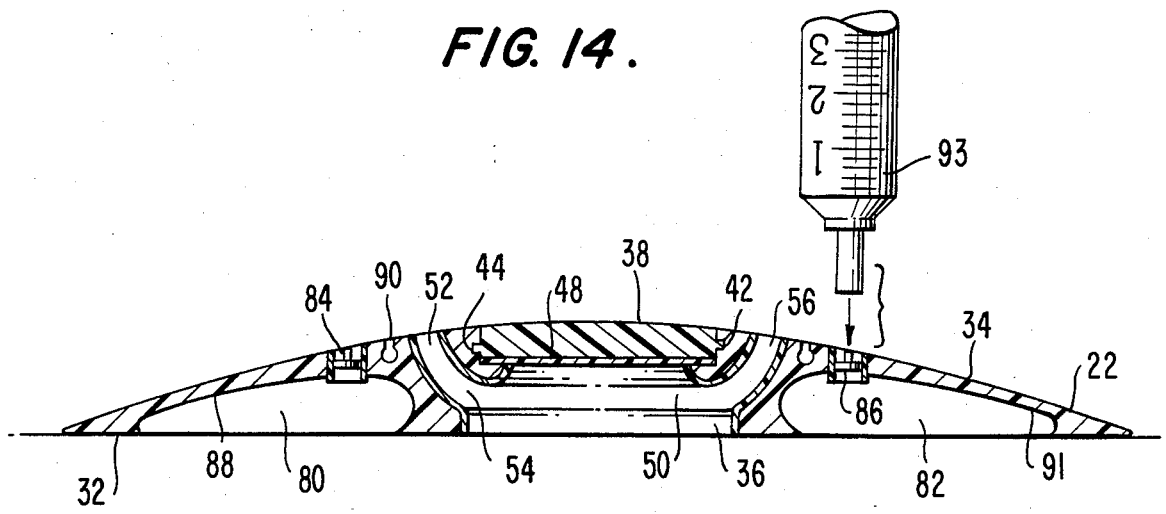
FIG. 14 is a cross-sectional view of the suction faceplate of FIG. 13 shown in place against the body before the vacuum has been applied.
Figure 15:
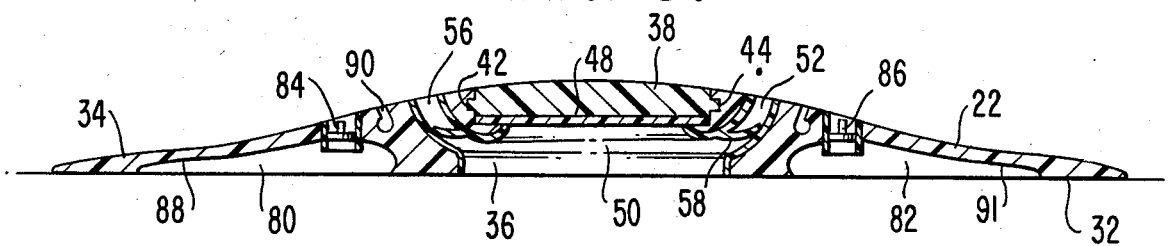
FIG. 15 is a view similar to FIG. 14 illustrating the suction faceplate after the vacuum has been applied.

Stoma protector shield 38 when threaded or snapped into its secure position is configured so that its lower surface 48, as best illustrated in FIGS. 4, 14 and 15 is spaced above the lower surface 32 of the faceplate and thus is spaced above the stoma when faceplate 22 is positioned on the user. A chamber 50 is thereby defined between the lower surface 48 of protector shield 38 and the stoma. A plurality of outflow channels 52 are provided communicating at their lower ends 54 with chamber 50 and at their upper outer end opening 56 with the outer surface 34 of the faceplate. The channels angle out away from the stoma, and one-way flap valves 58 can be built into the channels to prevent the reflux of the waste products back through channels 52 into the stoma. The size and shape of the openings 56 of the channels to the exterior of faceplate 22 are sized and configured for different waste products, such as is best shown in FIGS. 5 through 9, and are positioned around and outside of protector shield 38.

Figure 11:
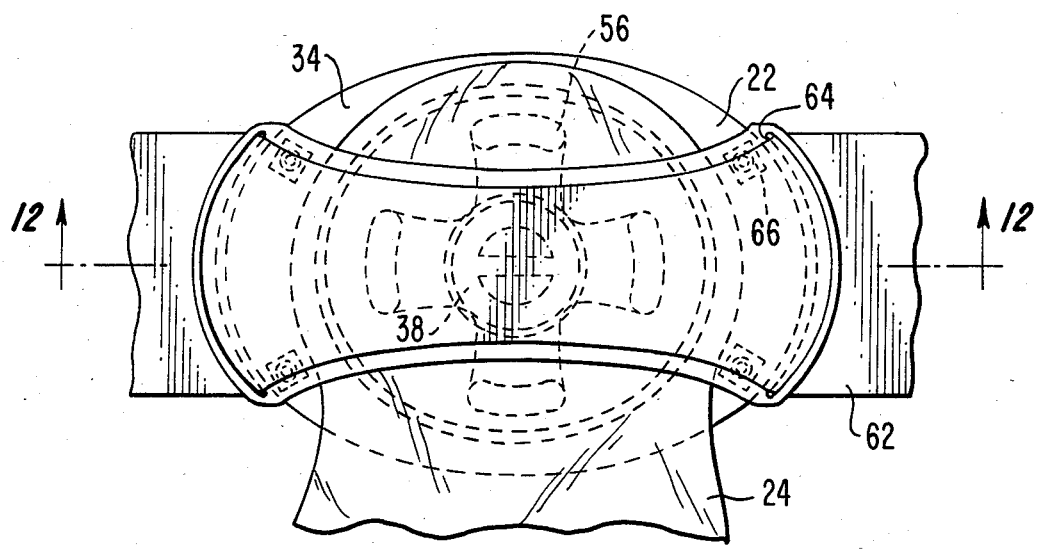
FIG. 11 is a front fragmentary view of an elliptical ostomy appliance of the present invention using an overlying brace strap.
Figure 12:
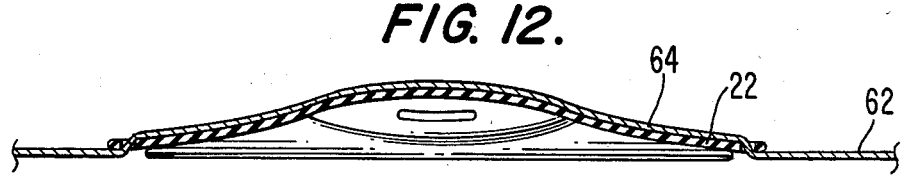
FIG. 12 is a cross-sectional view taken along line 12—12 of FIG. 11.

Adhesives are currently used for attaching the faceplates to the body of the user. However, when these prior art faceplates are removed frequently (as appropriate hygiene requires), even when great care is exercised and suitable solvent dissolvers are used, a tearing or irritation of the surrounding skin frequently results. In addition to damaging the skin, this can be a very painful process. Also, simple belts have been used to attach the faceplate to the wearer, but, if these are improperly worn, they can dislodge the faceplate. The present invention, on the other hand, provides for a novel means of attaching the faceplate to the body of the user over his stoma, which need not use adhesives. One embodiment of this novel means uses a brace strap system 60 as shown in FIGS. 6, 10, 11, and 12. Brace strap system 60 includes a belt 62 and a faceplate strap 64 adapted to be secured to the faceplate by nylon snaps 66 and to extend across the face of faceplate 22 and when worn applying an even pressure across the faceplate towards the user. When snapped in place the strap 60 is snapped outside of receptacle 24 as best shown in FIG. 11. The belt portion includes a cotton comfort surface 68 which is worn against the user's skin. The two ends of the belt are secured together by Velcro or hook closures 70 which are adjustable to accommodate the different waist sizes of the patients. Elastic inserts 72 add resiliency to the belt. Within portions of the belt an inner semi-flexible light plastic insert 74 is positioned in the flat-tubed shape outer member 76, as best shown in FIG. 10. These plastic inserts 74 prevent curling, rolling or kinking of the belt 62 while it is in place on the user. Additionally, the nonadhesive faceplates have a layer of cushion composite, soft, pliable, non-porous material shown at 78 in FIG. 4 secured to the lower surface of the faceplate directly in contact with the ostomate's skin, and when worn with brace strap system 60, it produces a maximal faceplate to body seal. Cushion composite 78 compresses slightly and resists slippage of the faceplate relative to the stoma to ensure optimal security for comfort and privacy. Brace strap system 60 provides improved stoma protection, security, and allows easy daily removal of the non-adhesive faceplates for excellent hygiene of appliance and stoma.

The present invention further includes novel ostomy underwear (not shown) for men, women and children which are compatible with the subject ostomy appliance 20 and brace strap system 60. These undergarments contain suitable snaps for securing the garment to the brace strap and an inner pouch to support the ostomy appliance receptacle. The ostomy underwear provides alternative pouch embodiments allowing the receptacle to be worn either in the groin or around the hip. The ostomy appliance receptacle sleeve (not shown) is an alternative to the appliance compatible undergarments, and can be designed in various sizes to be compatible with all ostomy appliance receptacles. Elastic material at the faceplate and drain valve openings produce a secure fit on ostomy appliances. Both appliance compatible undergarments and receptacle sleeves are made of cotton which is soft and comfortable, has excellent moisture absorption and is "breathable" allowing good air circulation around the ostomy appliance receptacle. Using either the receptacle sleeve or the ostomy compatible undergarment, the ostomy appliance wearer can avoid the chafing, skin irritation, moisture accumulation and possible fungal skin infection resulting from prolonged contact of plastic against moist skin, especially in the groin area, previously experienced by ostomates.

Figure 13:
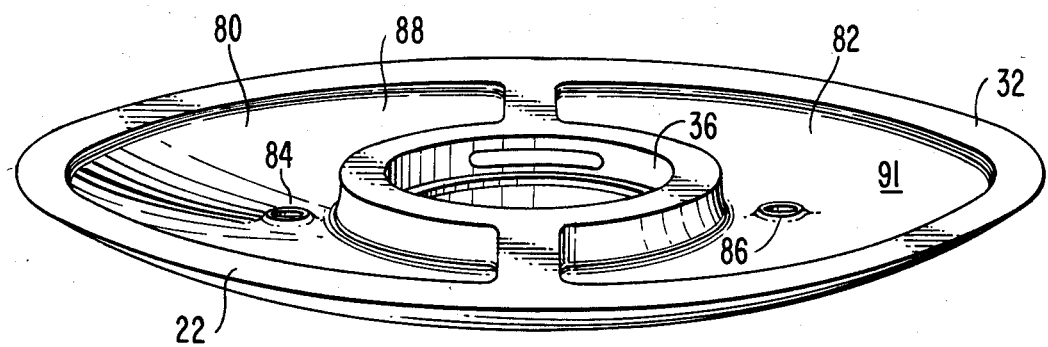
FIG. 13 is a bottom perspective view of a suction faceplate alternative of the present invention.

A suction system can be used to fix and hold the faceplate to the user's body, either in conjunction with the brace strap or in place of it. This is best illustrated in FIGS. 13, 14 and 15. Referring thereto, it is seen that suction faceplate 22 is provided with a pair of opposing inner chambers 80, 82, each having a one-way twist valve 84, 86 extending, respectively, from the faceplate outer surface 34 to their inner chamber 80, 82. It is also within the scope of the present invention to provide for three chambers as shown in FIG. 5 with three valves 84, 86, and 87 in a triangular faceplate 22 embodiment. Thus, when the faceplate is initially positioned over the stoma, as in FIG. 14, the chambers 80 and 82 are in their natural uninflated position with the chamber inner surfaces 88, 91 being defined by the user's body. A suction device 93 such as a standard Luer tip 50 cc. syringe is inserted into one-way twist valves 84, 86 and suction provided to the inner chambers 80, 82. This causes flexible suction faceplate 22 to be sucked towards the user and a partial vacuum thereby defined, as illustrated in FIG. 15, holding the suction faceplate to the user's body. An optimum faceplate to body seal can be maintained with this system by periodically using the syringe to reestablish the vacuum within the suction chambers. Suction faceplate 22 is appropriate for a variety of ostomy appliance wearers, including those individuals in hospitals with ostomies, recently created or revised ostomies, mucous fistulas and open or draining wounds. It is anticipated that this faceplate could be made available pre-packaged and sterile for use with newly-created ostomies and open wounds. This system of ostomy or wound care provides for easy daily or periodic access for appropriate hygiene and a marked reduction in chance contamination or cross contamination. Further, use of this system will avoid tape burns or skin maceration, often present with traditional adhesives and adhesive removers. Also, as a convalescent new ostomy patient's condition improves and he becomes more active, the previously-described brace strap 60 can be added to provide additional security.

Figure 2:
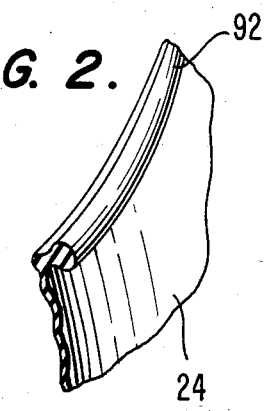
FIG. 2 is an enlarged sectional view taken on line 2—2 of FIG. 1.
Figure 3:
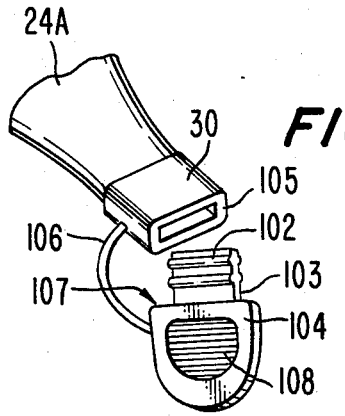
FIG. 3 is an enlarged sectional view taken on line 3—3 of FIG. 1 illustrated in the drain open position.

The groove attachment means 26 for easily attaching and removing receptacle 24 to faceplate 22 is best shown in FIGS. 1 and 2. It is seen therein that a groove 90 is provided in outer surface 34 of the faceplate encircling the upper surface opening 40, channel outer end openings 56 and protector shield 38. Receptacle 24 is similarly provided with a circular male member 92 best shown in FIG. 2 as including an elongated bulbous member which is adapted to fit or snap into the entire circumference of groove 90 and thereby secure receptacle 24 to faceplate 22. A flatter, slimmer contour of ostomy appliance 20 than was previously possible is thereby defined affording the ostomate with improved privacy. Additionally, a superior seal is thereby achieved with the present groove system than with prior systems affording the ostomate greater security against possible leakage. The groove system, perhaps most importantly, provides easy stoma access which together with the protector shield facilitates daily stoma hygiene.

Figure 16:
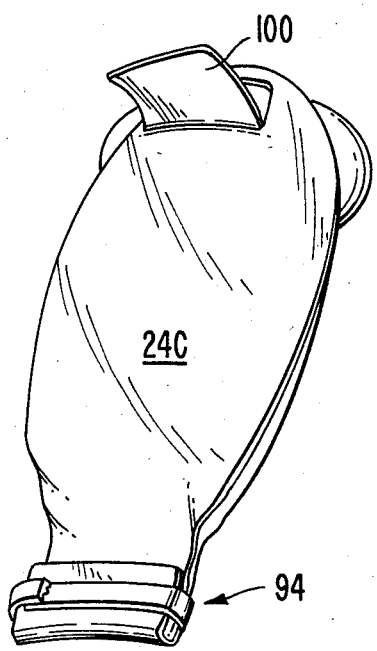
FIG. 16 is a perspective view of a second embodiment of the receptacle of FIG. 1.
Figure 17:
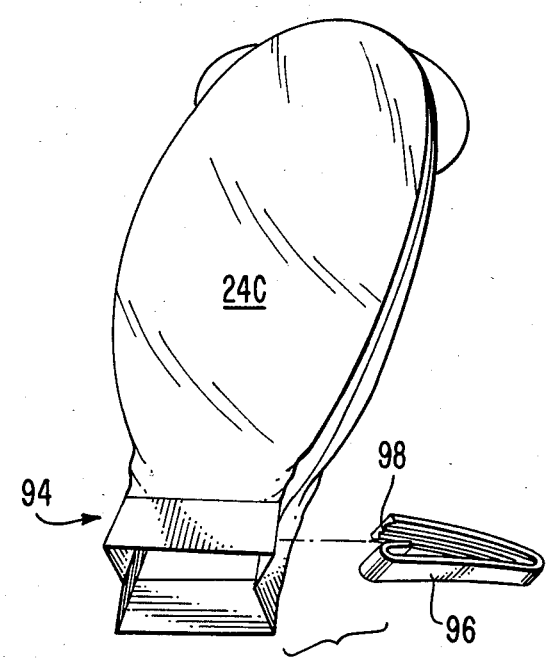
FIG. 17 is a perspective view of a modification of the receptacle of FIG. 16 with the clip shown in its open position.
Figure 18:
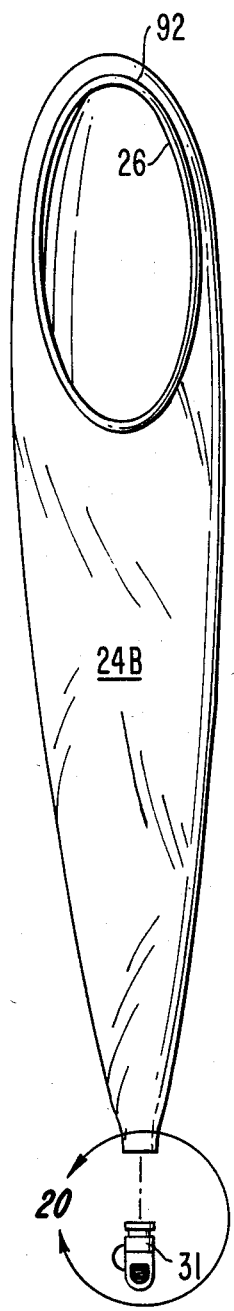
FIG. 18 is a perspective view of a disposable ostomy appliance receptacle with a detachable, reusable drain valve shown in exploded relation. Drain valve is in the closed position.
Figure 19:
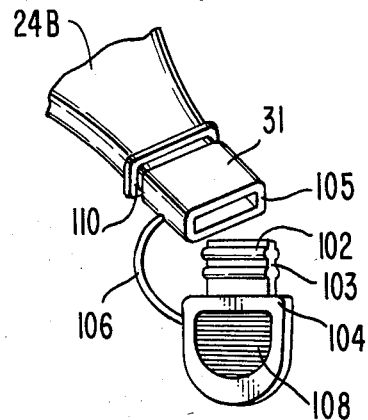
FIG. 19 is an enlarged sectional view taken online 5—5 of FIG. 18, illustrated in the drain open position with drain valve attached to receptacle using a rubber band.
Figure 20:
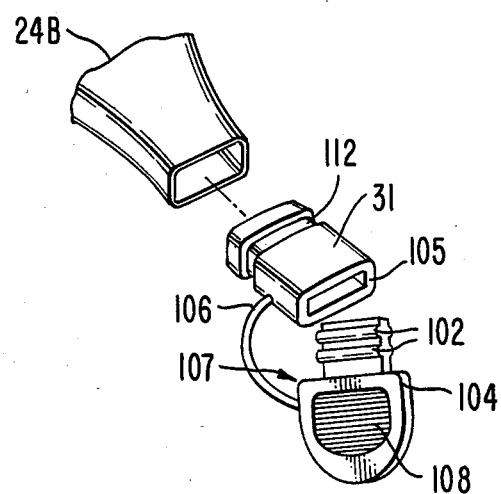
FIG. 20 is an enlarged sectional view taken on line 5—5 of FIG. 18 illustrated in the drain open position with reusable drain valve detached from receptacle.

Receptacles 24A, 24B, and 24C are designed for the present appliance. FIG. 1 shows a disposable receptacle 24A with a disposal drain valve 30 permanently attached for convenience and hygiene. An alternate receptacle 24B shown in FIGS. 18, 19 and 20 is a disposable receptacle with a detachable reusable drain valve 31 for reduced costs. Drain valve 31 is attached to receptacle 24B using rubber band 110, that seats in groove 112 as shown in FIGS. 19 and 20. These receptacles for ileostomy appliances are also available in both types 24A and 24B, and are appropriately larger than urostomy receptacles, with a correspondingly larger internal lumen of their drain valves 31. The colostomy appliance receptacle of FIGS. 16 and 17 are designed with a unique accordian type folding closure and clip assembly shown generally at 94 that eliminates the need for a separate drain valve. The clip 96 of the clip assembly has non-skid ribs 98 on its inner working surface. The receptacle of FIG. 16 has a resealable flap window or irrigation port 100 to allow colostomy irrigation while the receptacle is in place on the faceplate and the appliance secured to the user and in use. The resealing means for window or port 100 can be any suitable type, such as the groove system 26 of FIGS. 1 and 2 which seals the receptacle to the faceplate. It is anticipated receptacle 24 will be made of a soft flexible plastic material, highly resistant to leakage or puncture. They can be made available in sizes corresponding to the various faceplates and in a variety of opaque colors with or without clear plastic windows. With the receptacle of the present invention, lower bulging is minimized as any bulging is spread evenly by configuring the receptacle so that the widest part of the receptacle bag is above the lowest one-third portion of the length of the receptacle bag and the contents of a partially filled receptacle can be more eveny distributed throughout the volume of the receptacle.

All ostomy appliances have a method of periodic elimination of the waste products contained in the appliance receptacle. Presently, most of the ostomy appliances utilize a drain valve which is bulky and made of hard material with irregular contours. These currently available drain valves deny the appliance wearer his privacy, are uncomfortable and can cause injury to the wearer during a variety of physical activities, such as when horseback riding. The present drain valves 30 and 31 as shown in FIGS. 1, 3, 18, 19 and 20 have smaller exterior dimensions and smoothly contoured external edges with much slimmer overall profiles than prior art valves and are made of a softer flexible material. It thereby provides the wearer with greater privacy and comfort during a wide variety of physical activities than prior valves. Drain valve 30 is integral with the receptacle and drain valve 31 is detachable, as previously discussed. These valves will employ a double-locking plug mechanism, including double parallel ridges 102 in the male plug 104 that are designed to fit into the double parallel inner contours of the female valve. Plug 104 is thereby securely held in either valve 30 or 31. Leaks or dripping of these valves are prevented by the seal between the male portion 103 of plug 104 to the interior surfaces of valves 30 or 31 and by the seal between surface 105 of drain valves 30 or 31 and the base 107 of the plug handle 108. Plug 104 can be attached to the exterior of valve by a plastic lanyard 106, which prevents the plug from being dropped or lost. The plug handle 108 has a non-skid design to facilitate handling. As is evident, the present system can be operated conveniently by one hand.

In summary, there are many shortcomings and drawbacks among the wide variety of ostomy products currently available. The purposes of the present invention are to improve psychological adjustment, privacy, security, the ability to pursue a variety of physical activities, proper hygiene, prevention of infection, protection of the stoma and comfort for those who wear ostomy appliances. The products derived from the designs shown and described herein will facilitate daily life for the ostomate and allow ostomy appliance wearers to pursue active, fulfilling and productive lives without any limitations of activity.

From the foregoing detailed description, it will be evident that there are a number of changes, adaptations and modifications of the present invention which come within the province of those persons having ordinary skill in the art to which the aforementioned invention pertains. However, it is intended that all such variations not departing from the spirit of the invention be considered as within the scope thereof as limited solely by the appended claims.

I claim:

1. An ostomy appliance comprising:
   a faceplate having an inner surface, an opposite outer surface, and an opening engaging said inner surface,
   said faceplate being adapted to be placed so that said inner surface is generally against the body of a user and said opening registers with the stoma of the user,
   said faceplate including an outflow channel means communicating with said opening and engaging said outer surface for allowing the outflow of stoma waste products from the stoma through said faceplate,
   said faceplate further including a stoma protector shield having an inner shield surface adapted to face the user and an outer shield surface, said inner shield surface being positioned over said opening and spaced a small distance from said inner surface away from the user whereby a chamber is defined adjacent the stoma.
   said outflow channel means communicating with said chamber, and
   said protector shield being adapted to protect the stoma when an object impacts said faceplate at a location directly over the stoma.

2. The appliance of claim 1 including,
   said outflow channel means engaging said outer surface at a location outside of said protector shield away from the stoma.

3. The appliance of claim 1 including,
   said outer shield surface defining part of said outer surface.

4. The appliance of claim 1 including,
   said outflow channel means comprising at least two outflow channels engaging said outer surface at spaced locations.

5. The appliance of claim 4 including,
   said outflow channel means consisting of four generally independent, and spaced outflow channels.

6. The appliance of claim 1 including,
   said outflow channel means engaging said outer surface at an outer surface area,
   said faceplate including a shield support structure for supporting the outer edges of said stoma protector shield relative to said inner surface, and
   said shield support structure being positioned between said outer surface area and said inner surface.

7. The appliance of claim 1 including,
   said outflow channel means being oriented to angle from said inner surface towards said outer surface away from said opening.

8. The appliance of claim 1 including,
   said stoma protector shield being adapted to be movable away from said outer surface to provide access through said outer surface to the stoma for stoma hygiene cleaning when said faceplate is in position against the user.

9. The appliance of claim 8 including,
   said faceplate including a shield opening through said outer surface, over said opening, and in which said stoma protector shield is positionable, and a releasable securing means for releasably securing said stoma protector shield in said shield opening.

10. The appliance of claim 9 including,
    said releasable securing means including said shield opening having threaded members about its perimeter and said stoma protector shield having a threaded perimeter surface mated with an adapted to screw or snap into and out of said threaded members.

11. The appliance of claim 10 including,
    said stoma protector sheld including a member on said shield outer surface to be grasped by a user who is screwing or snapping said protector shield in or out of said shield opening.

12. The appliance of claim 1 including,
    said outflow channel means engaging said upper surface through at least one channel opening,
    a receptacle positionable adjacent said faceplate,
    said receptable having a receptacle opening, and
    a securing means for securing said receptacle securely to said faceplate such that said channel opening communicates through said receptacle opening into said receptacle.

13. The appliance of claim 12 including,
    a drain valve means connected permanently or reversibly to a lower end of said receptacle.

14. The appliance of claim 13 including,
    a generally flat drain valve female member having a plug opening with a pair of grooves therein, a generally flat plug male member having a pair of ridges thereon, said male member being configured to fit and seal in said drain valve opening with said ridges engaging in said grooves thereby providing a secure double locking effect, said male member having at least a portion of its exterior surface being rough to provide a non-skid means, and a lanyard means connecting said male member to said female member.

15. The appliance of claim 12 including,
    said securing means comprising an elongated female groove in said upper surface around said channel opening, and an elongated male member attached to said receptacle generally adjacent said receptacle opening, and said elongated male member being adapted to fit into said elongated female groove and thereby secure said receptacle to and around the entire perimeter of said receptacle opening to said faceplate.

16. The appliance of claim 1 including,
    said faceplate being generally flat and having a triangular shape.

17. The appliance of claim 1 including,
    said faceplate being generally flat and having an elliptical shape.

18. The appliance of claim 1 including, said inner surface being convex.

19. The appliance of claim 1 including, said inner surface being concave.

20. The appliance of claim 1 including, a layer of soft, pliable, non-porous material mounted to said lower surface and positionable directly adjacent the body of a user.

21. The appliance of claim 1 including a body securing means associated with said faceplate for securing said faceplate to the body of a user over his stoma.

22. The appliance of claim 21 including, said body securing means comprising a brace strap extending across the face of said faceplate over said protector shield and an attaching means on the external upper surface of said faceplate for attaching said brace strap to said upper surface.

23. The appliance of claim 1 including, a receptacle attachable to said faceplate, and said receptacle having an outer surface port for providing access to the stoma for irrigating the stoma through said receptacle and said faceplate, while in place on the user's body.

24. The appliance of claim 23 including, said outflow channel means including a one-way flap valve means for preventing the reflux of stoma urinary waste products from said receptacle or from said outer surface back into the stoma.

25. The appliance of claim 1 including, a Teflon coating on all surfaces of said faceplate that come into contact with the stoma waste products when said faceplate is secured to the body over the stoma.

26. The appliance of claim 1 including, a securing means for securing said faceplate to a user so that said inner surface is adjacent the body of the user and said opening is over the stoma of the user.

27. The appliance of claim 26 including, a receptacle having a receptacle opening, an attaching means for attaching said receptacle to said opposite outer surface so that said receptacle opening communicates with said opening, said faceplate having a faceplate face, and said securing means including a brace strap extending laterally across said face and exerting pressure across said face, a fastening means for fastening said brace strap to said faceplate, and a belt attachable at opposite ends to said brace strap and adapted to go around the body of the user.

28. The appliance of claim 27 including, said fastening means comprising a snap means.

29. The appliance of claim 28 including, said brace strap being formed of plastic.

30. The appliance of claim 27 including, said belt including an inner cotton surface, a first member connected at one end to said brace strap, an elongated flat tube, a semi-flexible insert positioned in said flat tube, and an elastic insert connecting said first member and said flat tube.

31. The appliance of claim 1 including, a receptacle having a receptacle opening registrable with said faceplate opening such that stoma waste products can pass through said faceplate opening and through said receptacle opening and into said receptable.

32. The appliance of claim 31 including, said receptacle opening passing through an upper portion of said receptacle, and said receptacle including a lower portion having a lower opening therethrough and adapted to fold over onto itself between an open position wherein stoma waste product can pass out through said lower opening for emptying said receptacle and a closed position folded over on itself wherein stoma waste product can be stored in said receptacle, and a clip means attachable to said lower portion when folded over on itself for securing said lower portion in said closed position.

33. The appliance of claim 32 including, said receptacle having an upper one third portion and a lower two thirds portion, said upper one third portion being wider than said lower two thirds portion.

34. The appliance of claim 32 including, a resealable flap in the outer side of the upper portion of said receptacle for providing access through said receptacle opening and said faceplate opening to the stoma for irrigating the stoma.

35. An ostomy appliance comprising: a faceplate having an inner surface, an opposite outer surface, an inner surface opening positionable over the stoma of a user, a channel means communicating said outer surface with said inner surface opening, an outer surface opening communicating with said inner surface, a portion of said outer surface comprising a movable access means movable away from the rest of said outer surface, when said faceplate is in position over the stoma, for providing access through said inner surface opening to the stoma for stoma hygiene purposes and subsequently movable back to a stoma protective normal position.

36. An ostomy appliance comprising: a faceplate having an inner surface, an opposite outer surface, and an opening engaging said inner surface, said faceplate being adapted to be placed so that said inner surface is generally against the body of a user and said opening registers with the stoma of the user, said faceplate including an outflow channel means communicating with said opening and engaging said outer surface for allowing the outflow of stoma waste products from the stoma through said faceplate, said faceplate further including a stoma protector shield having an inner shield surface adapted to face the user and be positioned over said opening, and an outer shield surface, said faceplate including a supporting means for supporting said protector shield away from the stoma and defining a protective chamber between said outer shield surface and the stoma when said faceplate is secured to the body over the stoma, said outflow channel means communicating with said protective chamber, and said protector shield being adapted to protect the stoma when an object impacts said faceplate at a location directly over the stoma.

* * * * *